United States Patent
Schlosberg et al.

(10) Patent No.: US 7,595,420 B2
(45) Date of Patent: *Sep. 29, 2009

(54) HYDROGENATION OF BENZENE POLYCARBOXYLIC ACIDS OR DERIVATIVES THEREOF

(75) Inventors: Richard Henry Schlosberg, Highland Park, IL (US); Jose Guadalupe Santiesteban, Baton Rouge, LA (US); Stuart L. Soled, Pittstown, NJ (US); Andrzej Mariusz Malek, Baton Rouge, LA (US); Joseph E. Baumgartner, Califon, NJ (US); Luo Shifang, Pittsford, NY (US); Sabato Miseo, Pittstown, NJ (US); James Clarke Vartuli, Schwenksville, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/535,531

(22) PCT Filed: Nov. 18, 2003

(86) PCT No.: PCT/EP03/12881

§ 371 (c)(1), (2), (4) Date: Jun. 2, 2006

(87) PCT Pub. No.: WO2004/046078

PCT Pub. Date: Jun. 3, 2004

(65) Prior Publication Data

US 2006/0247461 A1 Nov. 2, 2006

(30) Foreign Application Priority Data

Nov. 20, 2002 (GB) ................................. 0227087.4

(51) Int. Cl.
*C07C 69/74* (2006.01)
*C07C 62/00* (2006.01)
(52) U.S. Cl. ...................................... 560/127; 562/509
(58) Field of Classification Search ....................... None
See application file for complete search history.

(56) References Cited

U.S. PATENT DOCUMENTS

| 3,027,398 | A | 3/1962 | Foohey et al. | ................ 260/468 |
| 3,334,149 | A | 8/1967 | Akin et al. | .................... 260/617 |
| 5,286,898 | A | 2/1994 | Gustafson et al. | ............ 560/127 |
| 5,319,129 | A | 6/1994 | Gustafson et al. | ............ 560/127 |
| 5,936,126 | A | 8/1999 | Ruhl et al. | .................... 564/451 |
| 6,248,924 | B1 | 6/2001 | Ruhl et al. | .................... 564/450 |
| 6,284,917 | B1 * | 9/2001 | Brunner et al. | .............. 560/127 |

FOREIGN PATENT DOCUMENTS

| EP | 0 005 737 | 2/1979 |
| EP | 0 603 825 | 2/1998 |
| WO | WO 99/32427 | 1/1999 |

OTHER PUBLICATIONS

Raja et al., Angewandte Chemie, International Edition (2001), 40(24), 4638-4642.*

* cited by examiner

*Primary Examiner*—Karl J Puttlitz
(74) *Attorney, Agent, or Firm*—Andrew B. Griffis

(57) ABSTRACT

A process for hydrogenating benzenepolycarboxylic acids or derivatives thereof, such as esters and/or anhydrides, by bringing one or more benzenepolycarboxylic acids or one or more derivatives thereof into contact with a hydrogen-containing gas in the presence of one or more catalytically active metal, such as platinum, palladium, ruthenium or mixtures thereof, deposited on a catalyst support comprising one or more ordered mesoporous materials.

45 Claims, No Drawings

HYDROGENATION OF BENZENE POLYCARBOXYLIC ACIDS OR DERIVATIVES THEREOF

CROSS REFERENCE TO RELATED APPLICATIONS

This application is a National Stage Application of International Application No. PCT/EP2003/012881, filed 18 Nov. 2003, which claims benefit of Great Britain Application No. 0227087.4, filed 20 Nov. 2002. These applications are incorporated herein by reference.

FIELD OF INVENTION

The present invention relates to a process for the hydrogenation of benzenepolycarboxylic acids or derivatives thereof, such as esters and/or anhydrides, and in particular to a hydrogenation process, which utilizes a catalyst based on the combination of one or more catalytically active metals with one or more ordered mesoporous materials as support.

BACKGROUND OF THE INVENTION

Hydrogenation is an established process both in the chemical and petroleum refining industries. Hydrogenation is conventionally carried out in the presence of a catalyst, which usually comprises a metal hydrogenation component deposited on a porous support material. The metal hydrogenation component is often nickel or one or more metals such as platinum, palladium, rhodium or ruthenium.

Hydrogenated derivatives of benzenepolycarboxylic acids or derivatives thereof, such as esters and/or anhydrides, have many uses. Of particular interest is their use as plasticisers for polymeric materials. In this context the dialkylhexahydrophthalates are an example of one class of these compounds that are of particular interest. These materials may be produced by hydrogenation of the corresponding phthalic acid ester in the presence of hydrogen and an active metal hydrogenation catalyst deposited on a support.

In U.S. Pat. No. 5,286,898 and U.S. Pat. No. 5,319,129, dimethylterephthalate is hydrogenated at $\geq 140°$ C. and a pressure of from 50 to 170 bar over supported Pd catalysts, which are treated with Ni, Pt and/or Ru to give the corresponding dimethylhexahydroterephthalate. The supports used are alumina of crystalline phase alpha or theta or delta or gamma or beta or mixtures thereof.

In EP-A-0 005 737, aromatic carboxylic esters are hydrogenated at from 70 to 250° C. and from 30 to 200 bar over supported Ni, Ru, Rh and/or Pd catalysts to give the corresponding cycloaliphatic carboxylic esters. The support used is an aluminium oxide of which at least 20% has been converted into lithium-aluminium spine.

U.S. Pat. No. 3,027,398 describes the hydrogenation of dimethylterephthalate over supported Ru catalysts at from 110 to 140° C. and from 35 to 105 bar. The Ru is deposited on charcoal or kieselguhr.

EP-A 0 603 825 relates to a process for the preparation of 1,4-cycylohexanedicarboxylic acid by hydrogenating terephthalic acid by using a supported palladium catalyst, wherein as support alumina, silica or active charcoal is used.

U.S. Pat. No. 3,334,149 describes a multistage process for the hydrogenation of dialkylterephthalate using a Pd catalyst followed by use of a copper chromite catalyst.

U.S. Pat. No. 5,936,126 describes a process for the hydrogenation of an aromatic compound. The catalyst used contains ruthenium as active metal alone or optionally with one or more other Group IB, VIIB or VIIIB metals on a macroporous support. The macroporous support exhibits an average pore diameter of at least 50 nm and a BET surface area of not more than about 30 $m^2/g$.

U.S. Pat. No. 6,248,924 describes a process for reacting organic compounds. The catalyst used contains ruthenium as active metal alone or optionally with one or more other Group IB, VIIB or VIIIB metals on a support. The support may be a material having macropores (50 to 10000 nm pore diameter) and mesopores (2 to 50 nm pore diameter). In the support 10-50% of the pores are macropores and 50 to 90% of the pores are mesopores. Alumina of surface area (BET) 238 $m^2/g$ is specifically exemplified.

Published International Application No. PCT/EP98/08346 (WO 99/32427) describes a process for the hydrogenation of benzene polycarboxylic acids or derivatives thereof. The catalyst used comprises ruthenium as an active metal which is deposited alone or together with at least one other metal of subgroups I, VII or VIII of the periodic table on a support. One of three separate types of support may be used. The first support is macroporous having a mean pore diameter of at least about 50 nm and a BET surface area of at most 30 $m^2/g$. The second support is a material, which has both macropores and mesopores (2 to 50 nm pore diameter), and in which 5-50% of the pores are macropores, 50 to 95% of the pores are mesopores and the surface area of the support is preferably from 50 to about 500 $m^2/g$. The third type of support is a material, which is macroporous and has a mean pore diameter of at least 0.1 lm and a surface area of at most 15 $m^2/g$.

Of particular importance in the hydrogenation of benzenepolycarboxylic acids or derivatives thereof is the degree of conversion of the starting materials and the selectivity of conversion into the desired hydrogenated cyclohexyl derivatives. The degree of conversion should be as high as possible and typically conversion levels of greater than 95% are sought and achieved for these types of hydrogenation. However, in these types of hydrogenation whilst high conversions may be obtained it is difficult to simultaneously achieve the required high degree of selectivity to the desired product. In this regard there is a problem with the generation of low molecular weight and/or boiling point by-products during the hydrogenation reaction. These by-products are often referred to as "lights" and they must be removed from the hydrogenation product before it is used for example as a plasticiser.

There is a need therefore for new hydrogenation processes for the conversion of benzenepolycarboxylic acids or derivatives to the corresponding ring-hydrogenated derivatives, which produce lower levels of "lights" by-products and thus result in improved selectivity for the desired products. It is therefore, an object of the present invention to provide a process for hydrogenating benzenedicarboxylic esters or anyhdrides, using specific catalysts, by means of which the corresponding, hydrogenation products may be obtained with high levels of conversion and selectivity.

SUMMARY OF THE INVENTION

The present invention accordingly provides a process for hydrogenating one or more benzenepolycarboxylic acids or one or more derivatives thereof, or a mixture of one or more benzenepolycarboxylic acids or one or more derivatives thereof by bringing the benzenepolycarboxylic acid or the derivative thereof or the mixture into contact with a hydrogen-containing gas in the presence of a catalyst, the catalyst comprising one or more catalytically active metals applied to a catalyst support comprising one or more ordered mesoporous materials.

In a further aspect the catalyst support comprises one or more macroporous materials combined in admixture with the one or more ordered mesoporous materials.

In a further aspect the catalyst support comprises one or more mixed porosity materials combined in admixture with the one or more ordered mesoporous materials.

In a further aspect the catalyst comprises as active metal at least one metal of transition group VIII of the Periodic Table either alone or together with at least one metal of transition group I or VII of the Periodic Table.

DETAILED DESCRIPTION OF THE INVENTION

In the process of the present invention benzenepolycarboxylic acids or derivatives thereof are hydrogenated to the corresponding cyclohexyl derivative in the presence of hydrogen and a catalyst comprising an active hydrogenation metal component deposited on one or more ordered mesoporous materials. We have found that a certain class of support materials, namely ordered mesoporous materials, which have high pore volume, high surface area and controlled pore openings of at least 2 nm, are particularly suitable for the hydrogenation of benzenepolycarboxylic acids or derivatives thereof.

The term "benzenepolycarboxylic acid or a derivative thereof" used for the purposes of the present invention encompasses all benzenepolycarboxylic acids as such, e.g. phthalic acid, isophthalic acid, terephthalic acid, trimellitic acid, trimesic acid, hemimellitic acid and pyromellitic acid, and derivatives thereof, particularly monoesters, diesters and possibly triesters and tetraesters, in particular alkyl esters, and anhydrides such as phthalic anhydride or trimellitic anhydride or their esters. The esters used are alkyl, cycloalkyl and alkoxyalkyl esters, where the alkyl, cycloalkyl and alkoxyalkyl groups generally have from 1 to 30, preferably from 2 to 20 and particularly preferably from 3 to 18, carbon atoms and can be branched or linear.

One class of suitable benzenepolycarboxylic acids or a derivatives thereof are the alkyl terephthalates such as monomethyl terephthalate, dimethyl terephthalate, diethyl terephthalate, di-n-propyl terephthalate, di-n-butyl terephthalate, di-tert-butyl terephthalate, diisobutyl terephthalate, monoglycol esters of terephthalic acid, diglycol esters of terephthalic acid, di-n-octyl terephthalate, diisooctyl terephthalate, mono-2-ethylhexyl terephthalate, di-2-ethylhexyl terephthalate, di-n-nonyl terephthalate, diisononyl terephthalate, di-n-decyl terephthalate, di-n-undecyl terephthalate, diisodecyl terephthalate, diisoundecyl terephthalate, diisododecyl terephthalate, di-n-octadecyl terephthalate, diisooctadecyl terephthalate, di-n-eicosyl terephthalate, ditridecyl terephthalate, diisotridecyl terephthalate, monocyclohexyl terephthalate and or dicyclohexyl terephthalate. Also suitable are derivates in which the alkyl groups of the ester groups are different alkyl groups. Mixtures of one or more alkyl terephthalates may be used.

Another suitable class are the alkyl phthalates such as monomethyl phthalate, dimethyl phthalate, diethyl phthalate, di-n-propyl phthalate, di-n-butyl phthalate, di-tert-butyl phthalate, diisobutyl phthalate, monoglycol esters of phthalic acid, diglycol esters of phthalic acid, di-n-octyl phthalate, diisooctyl phthalate, di-2-ethylhexyl phthalate, di-n-nonyl phthalate, diisononyl phthalate, di-n-decyl phthalate, diisodecyl phthalate, di-n-undecyl phthalate, di-isoundecyl phthalate, diisododecyl phthalate, di-n-octadecyl phthalate, diisooctadecyl phthalate, di-n-eicosyl phthalate, monocyclohexyl phthalate, dicyclohexyl phthalate, alkyl isophthalates such as monomethyl isophthalate, dimethyl isophthalate, diethyl isophthalate, di-n-propyl isophthalate, di-n-butyl isophthalate, di-tert-butyl isophthalate, diisobutyl isophthalate, monoglycol esters of isophthalic acid, diglycol esters of isophthalic acid, di-n-octyl isophthalate, diisooctyl isophthalate, di-2-ethylhexyl isophthalate, di-n-nonyl isophthalate, diisononyl isophthalate, di-n-decyl isophthalate, diisodecyl isophthalate, di-n-undecyl isophthalate, di-isoundecyl isophthalate, diisododecyl isophthalate, di-n-octadecyl isophthalate, diisooctadecyl isophthalate, di-n-eicosyl isophthalate, monocyclohexyl isophthalate and or dicyclohexyl isophthalate. Also suitable are derivates in which the alkyl groups of the ester groups are different alkyl groups. Mixtures of one or more alkyl phthalates or isophthalates may be used.

A further suitable class are the alkyl trimellitates such as monomethyl trimellitate, dimethyl trimellitate, diethyl trimellitate, di-n-propyl trimellitate, di-n-butyl trimellitate, di-tert-butyl trimellitate, diisobutyl trimellitate, the monoglycol ester of trimellitic acid, diglycol esters of trimellitic acid, di-n-octyl trimellitate, diisooctyl trimellitate, di-2-ethylhexyl trimellitate, di-n-nonyl trimellitate, diisononyl trimellitate, di-n-decyl trimellitate, diisodecyl trimellitate, di-n-undecyl trimellitate, di-isoundecyl trimellitate, diisododecyl trimellitate, di-n-octadecyl trimellitate, diisooctadecyl trimellitate, di-n-eicosyl trimellitate, monocyclohexyl trimellitate, dicyclohexyl trimellitate and trimethyl trimellitate, triethyl trimellitate, tri-n-propyl trimellitate, tri-n-butyl trimellitate, tri-tert-butyl trimellitate, triisobutyl trimellitate, triglycol esters of trimellitic acid, tri-n-octyl trimellitate, triisooctyl trimellitate, tri-2-ethylhexyl trimellitate, tri-n-nonyl trimellitate, tri-isononyl trimellitate, tri-n-decyl trimellitate, triisododecyl trimellitate, tri-n-undecyl trimellitate, tri-isoundecyl trimellitate, triisododecyl trimellitate, tri-n-octadecyl trimellitate, triisooctadecyl trimellitate, tri-n-eicosyl trimellitate and tricyclohexyl trimellitate. Also suitable are derivates in which the alkyl groups of the ester groups are different alkyl groups. Mixtures of one or more alkyl trimellitates may be used.

Also suitable are the alkyl trimesates such as monomethyl trimesate, dimethyl trimesate, diethyl trimesate, di-n-propyl trimesate, di-n-butyl trimesate, di-tert-butyl trimesate, diisobutyl trimesate, monoglycol esters of trimesic acid, diglycol esters of trimesic acid, di-n-octyl trimesate, diisooctyl trimesate, di-2-ethylhexyl trimesate, di-n-nonyl trimesate, diisononyl trimesate, di-n-decyl trimesate, diisodecyl trimesate, di-n-undecyl trimesate, di-isoundecyl trimesate, diisododecyl trimesate, di-n-octadecyl trimesate, diisooctadecyl trimesate, di-n-eicosyl trimesate, monocyclohexyl trimesate, dicyclohexyl trimesate, and also trimethyl trimesate, triethyl trimesate, tri-n-propyl trimesate, tri-n-butyl trimesate, tri-tert-butyl trimesate, triisobutyl trimesate, triglycol esters of trimesic acid, tri-n-octyl trimesate, triisooctyl trimesate, tri-2-ethyl-hexyl trimesate, tri-n-nonyl trimesate, tri-isononyl trimesate, tri-n-decyl trimesate, triisododecyl trimesate, tri-n-undecyl trimesate, tri-isoundecyl trimesate, triisododecyl trimesate, tri-n-octadecyl trimesate, triisooctadecyl trimesate, tri-n-eicosyl trimesate and tricyclohexyl trimesate. Also suitable are derivates in which the alkyl groups of the ester groups are different alkyl groups. Mixtures of one or more alkyl trimesates may be used A further suitable class are the alkyl hemimellitates such as monomethyl hemimellitate, dimethyl hemimellitate, diethyl hemimellitate, di-n-propyl hemimellitate, di-n-butyl hemimellitate, di-tert-butyl hemimellitate, diisobutyl hemimellitate, monoglycol esters of hemimellitic acid, diglycol esters of hemimellitic acid, di-n-octyl hemimellitate, diisooctyl hemimellitate, di-2-ethylhexyl hemimellitate, di-n-nonyl hemimellitate, diisononyl hemimellitate, di-n-decyl hemimellitate, diisodecyl hemimellitate, di-n-undecyl hemimellitate, di-isoundecyl hemimellitate, diisododecyl hemimellitate, di-n-octadecyl hemimellitate, diisooctadecyl hemimellitate, di-n-eicosyl hemimellitate, monocyclohexyl hemimellitate, dicyclohexyl hemimellitate, and also trimethyl hemimellitate, triethyl hemimellitate, tri-n-propyl hemimellitate, tri-n-butyl hemimellitate, tri-tert-butyl hemimellitate, triisobutyl hemimellitate, triglycol esters of hemimellitic acid, tri-n-octyl hemimellitate, triisooctyl hemimellitate, tri-2-ethylhexyl hemimellitate, tri-n-nonyl hemimellitate, tri-isononyl hemimellitate, tri-n-decyl hemimellitate, triisodecyl hemimellitate, tri-n-undecyl hemimellitate, tri-isoundecyl hemimellitate, triisododecyl hemimellitate, tri-n-octadecyl hemimellitate, triisooctadecyl hemimellitate, tri-n-eicosyl hemimellitate and tricyclohexyl hemimellitate. Also suitable are derivates in which the alkyl groups of the ester groups are different alkyl groups. Mixtures of one or more alkyl hemimellitates may be used Another suitable class are the alkyl pyromellitates such as monomethyl pyromellitate, dimethyl pyromellitate, diethyl pyromellitate, di-n-propyl pyromellitate, di-n-butyl pyromellitate, di-tert-butyl pyromellitate, diisobutyl pyromellitate, monoglycol esters of pyromellitic acid, diglycol esters of pyromellitic acid, di-n-octyl pyromellitate, diisooctyl pyromellitate, di-2-ethylhexyl pyromellitate, di-n-nonyl pyromellitate, diisononyl pyromellitate, di-n-decyl pyromellitate, diisodecyl pyromellitate, di-n-undecyl pyromellitate, di-isoundecyl pyromellitate, diisododecyl pyromellitate, di-n-octadecyl pyromellitate, diisooctadecyl pyromellitate, di-n-eicosyl pyromellitate, monocyclohexyl pyromellitate, trimethyl pyromellitate, triethyl pyromellitate, tri-n-propyl pyromellitate, tri-n-butyl pyromellitate, tri-tert-butyl pyromellitate, triisobutyl pyromellitate, triglycol esters of pyromellitic acid, tri-n-octyl pyromellitate, triisooctyl pyromellitate, tri-2-ethylhexyl pyromellitate, tri-n-nonyl pyromellitate, tri-isononyl pyromellitate, triisodecyl pyromellitate, tri-n-decyl pyromellitate, tri-n-undecyl pyromellitate, tri-isoundecyl pyromellitate, triisododecyl pyromellitate, tri-n-octadecyl pyromellitate, triisooctadecyl pyromellitate, tri-n-eicosyl pyromellitate, tricyclohexyl pyromellitate, and also tetramethyl pyromellitate, tetraethyl pyromellitate, tetra-n-propyl pyromellitate, tetra-n-butyl pyromellitate, tetra-tert-butyl pyromellitate, tetraisobutyl pyromellitate, tetraglycol esters of pyromellitic acid, tetra-n-octyl pyromellitate, tetraisooctyl pyromellitate, tetra-2-ethylhexyl pyromellitate, tetra-n-nonyl pyromellitate, tetraisododecyl pyromellitate, tetra-n-undecyl pyromellitate, tetraisododecyl pyromellitate, tetra-n-octadecyl pyromellitate, tetraisooctadecyl pyromellitate, tetra-n-eicosyl pyromellitate, tetracyclohexyl pyromellitate. Also suitable are derivates in which the alkyl groups of the ester groups are different alkyl groups. Mixtures of one or more alkyl pyromellitates may be used.

Also suitable are anhydrides of phthalic acid, trimellitic acid, hemimellitic acid and pyromellitic acid.

Also suitable are alkyl terephthalates, alkyl phthalates, alkyl isophthalates, dialkyl or trialkyl trimellitates, dialkyl or trialkyl trimesates, dialkyl or trialkyl hemimellitates and dialkyl, trialkyl or tetraalkyl pyromellitates in which one or more of the alkyl groups contain 5, 6 or 7 carbon atoms (e.g. are $C_5$, $C_6$ or $C_7$ alkyl groups) such alkyl groups include; n-pentyl, 1-methylbutyl terephthalate, 2-methylbutyl, 3-methylbutyl, 2,2-dimethylpropyl, 1,1-dimethylpropyl, n-hexyl, 1-methylpentyl, 2-methylpentyl, 3-methylpentyl, 4-methylpentyl, 1,1-dimethylbutyl, 2,2-dimethylbutyl, 3,3-dimethylbutyl, 1,2-dimethylbutyl, 1,3-dimethylbutyl, 2,3-dimethylbutyl, 1-methyl-2-ethylpropyl, 1-ethyl-2-methylpropyl, 1-ethylbutyl, 2-ethylbutyl, n-heptyl, 1-methylhexyl, 2-methylhexyl, 3-methylhexyl, 4-methylhexyl, 5-methylhexyl, 1,1-dimethylpentyl, 2,2-dimethylpentyl, 3,3-dimethylpentyl, 4,4-dimethylpentyl, 1-ethylpentyl, 2-ethylpentyl, 3-ethylpentyl, 1,1,2-trimethylbutyl, 1,1,3-trimethylbutyl, 1,2,2-trimethylbutyl, 2,2,3-trimethylbutyl, 1,3,3-trimethylbutyl, 2,3,3-trimethylbutyl, 1,2,3-trimethylbutyl, 1-ethyl-2-methylbutyl, 1-ethyl-3-methylbutyl, 2-ethyl-3-methylbutyl and 1-methyl-2-ethylbutyl. Also envisaged as suitable are compounds in which the alkyl groups are not identical such as for example in butylpropyl terephthalate or where one of the alkyl groups is replaced by a benzyl group such as for example in butylbenzyl terephthalate. Also suitable are mixtures of one or more alkyl terephthalates, alkyl phthalates, alkyl isophthalates, dialkyl or trialkyl trimellitates, dialkyl or trialkyl trimesates, dialkyl or trialkyl hemimellitates and dialkyl, trialkyl or tetraalkyl pyromellitates in which one or more of the alkyl groups contain 5, 6 or 7 carbon atoms.

In the process of the present invention it is also possible to use mixtures of one or more of the benzenepolycarboxylic acid or a derivative thereof described herein. When the derivatives are esters the mixture may be derived through use of a two or more alcohols in admixture or in sequence to esterify the same sample of a benzenepolycarboxylic acid derivative or a mixture of two or more benzenepolycarboxylic acids or a derivatives. Alternatively the alcohols may be used to form, in separate syntheses, two different esterified derivatives, which may then be mixed together to form a mixture of two or more esterified derivatives. In either approach the mixture may comprise a mixture of esters derived from branched or linear alcohols, for example the mixture may comprise ester derivatives prepared from C7, C9, C8, C10 and C11 linear or branched alcohols, preferably linear alcohols, with the alcohols being used in the same synthesis of a mixture of derivatives or in separate syntheses of the derivative where the resultant derivative products in each synthesis are combined to form a mixed derivative.

In the process of the present invention the preferred products are those derived from phthalates and in particular the following: cyclohexane-1,2-dicarboxylic acid di(isopentyl) ester, obtainable by hydrogenation of a di(isopentyl) phthalate having the Chemical Abstracts registry number (in the following: CAS No.) 84777-06-0; cyclohexane-1,2-dicarboxylic acid di(isoheptyl) ester, obtainable by hydrogenating the di(isoheptyl) phthalate having the CAS No. 71888-89-6; cyclohexane-1,2-dicarboxylic acid di(isononyl) ester, obtainable by hydrogenating the di(isononyl)phthalate having the CAS No. 68515-48-0; cyclohexane-1,2-dicarboxylic acid di(isononyl) ester, obtainable by hydrogenating the di(isononyl)phthalate having the CAS No. 28553-12-0, which is based on n-butene; cyclohexane-1,2-dicarboxylic acid di(isononyl) ester, obtainable by hydrogenating the di(isononyl)phthalate having the CAS No. 28553-12-0, which is based on isobutene; a 1,2-di-$C_9$-ester of cyclohexanedicarboxylic acid, obtainable by hydrogenating the di(nonyl)phthalate having the CAS No. 68515-46-8; cyclohexane-1,2-dicarboxylic acid di(isodecyl) ester, obtainable by hydrogenating a di(isodecyl)phthalate having the CAS No. 68515-49-1; 1,2-$C_{7-11}$-ester of cyclohexanedicarboxylic acid, obtainable by hydrogenating the corresponding phthalic acid ester having the CAS No. 68515-42-4; 1,2-di-$C_{7-11}$-ester of cyclohexanedicarboxylic acid, obtainable by hydrogenating the di-$C_{7-11}$-phthalates having the following CAS Nos.: 111381-89-6, 111381-90-9, 111381-91-0, 68515-44-6, 68515-45-7 and 3648-20-7; a 1,2-di-$C_{9-11}$-ester of cyclohexanedicarboxylic acid, obtainable by hydrogenating a di-$C_{9-11}$-phthalate having the CAS No. 98515-43-5; a 1,2-di(isodecyl)cyclohexanedicarboxylic acid ester, obtainable by hydrogenating a di(isodecyl)phthalate, consisting essentially of di-(2-propylheptyl)phthalate; 1,2-di-$C_{7-9}$-cyclohexanedicarboxylic acid ester, obtainable by hydrogenating the corresponding phthalic acid ester, which comprises branched and linear $C_{7-9}$-alkylester groups; respective phthalic acid esters which may be e.g. used as starting materials have the following CAS Nos.: di-$C_{7-9}$-alkylphthalate having the CAS No. 111 381-89-6; di-$C_7$-alkylphthalate having the CAS No. 68515-44-6; and di-$C_9$-alkylphthalate having the CAS No. 68515-45-7.

More preferably, the above explicitly mentioned $C_{5-7}$, $C_9$, $C_{10}$, $C_{7-11}$, $C_{9-11}$ and $C_{7-9}$ esters of 1,2-cyclohexanedicarboxylic acids are preferably the hydrogenation products of the commercially available benzenepolycarboxylic acid esters with the trade names Jayflex® DINP (CAS No. 68515-48-0), Jayflex® DIDP (CAS No. 68515-49-1), Jayflex® DIUP (CAS No. 85507-79-5), Jayflex® DTDP (CAS No. 68515-47-9), Palatinol® 911P, Vestinol® 9 (CAS No. 28553-12-0), TOTM-I® (CAS No. 3319-31-1), Linplast® 68-TM and Palatinol® N (CAS No. 28553-12-0) which are used as plasticizers in plastics.

Further examples of commercially available benzenepolycarboxylic acid esters suitable for use in the present invention include phthalates such as: Palatinol® AH (Di-(2-ethylhexyl) phthalate; Palatinol® AH L (Di-(2-ethylhexyl) phthalate); Palatinol® C (Dibutyl phthalate); Palatinol® IC (Diisobutyl phthalate); Palatinol® N (Diisononyl phthalate); Palatinol® Z (Diisodecyl phthalate) Palatinol® 10-P (Di-(2-Propylheptyl) phthalate); Palatinol® 711P (Heptylundecyl phthalate); Palatinol® 911 (Nonylundecyl phthalate); Palatinol® 11P-E (Diundecyl phthalate); Palatinol® M (Dimethyl phthalate); Palatinol® A (Diethyl phthalate); Palatinol® A (R) (Diethyl phthalate); and Palatinol® K (Dibutylglycol phthalate). Further examples are the commercially available adipates such as: Plastomoll® DOA (Di-(2-ethylhexyl) adipate) and Plastomoll® DNA (Diisononyl adipate). Further examples of suitable commercially available materials are Vestinol® C (DBP), Vestinol® IB (DIBP), Vestinol® AH (DEHP), Witamol® 110 (610P) and Witamol® 118 (810P).

For the purposes of the present invention, the terms "macropores" and "mesopores" are used as they are defined in Pure Appl. Chem., 45 (1976), 79, namely as pores whose diameter is above 50 nm (macropores) or whose diameter is from 2 nm and 50 nm (mesopores). In the process of the present invention the one or more catalytically active metals are deposited on a specific catalyst support. This catalyst support is prepared from one or more ordered mesoporous materials.

Preferred ordered mesoporous materials that may be used in the present invention, are those ordered mesoporous materials that may be synthesized using amphiphilic compounds as directing agents. Examples of such materials are described in U.S. Pat. No. 5,250,282, the whole contents of which are hereby incorporated by reference. Examples of amphiphilic compounds are also provided in Winsor, Chemical Reviews, 68(1), 1968. Other suitable ordered mesoporous materials of this type are also described in "Review of Ordered Mesoporous Materials", U. Ciesla and F. Schuth, Microporous and Mesoporous Materials, 27, (1999), 131-49. Such materials include but are not limited to materials designated as SBA (Santa Barbara) such as SBA-2, SBA-15 and SBA-16, materials designated as FSM (Folding Sheet Mechanism) such as FSM-16 and KSW-2, materials designated as MSU (Michigan State) such as MSU-S and MSU-X, materials designated as TMS or Transition Metal Sieves, materials designated as FMMS or functionalized monolayers on mesoporous supports and materials designated as APM or Acid Prepared Mesostructure. Particularly preferred ordered mesoporous materials are the silicate or aluminosilicate ordered mesoporous materials designated as M41S such as MCM-41, MCM-48 and MCM-50. These ordered mesoporous materials are described in detail in U.S. Pat. No. 5,102,643, the whole contents of which are hereby incorporated by reference. A particularly suitable sub-class of this family of materials for use in the present invention are the mesoporous silicas designated as MCM-41 and MCM-48. MCM-41 is particularly preferred and has a hexagonal arrangement of uniformly sized mesopores. MCM-41 molecular sieve materials are described in detail in U.S. Pat. No. 5,098,684, the whole contents of which are hereby incorporated by reference. The MCM-41 molecular sieves generally have a $SiO_2/Al_2O_3$ molar ratio when alumina is present that is greater than 100, preferably greater than 200, and most preferably greater than 300.

In the present invention, the hydrogenation process utilizes a catalyst, which comprises a hydrogenation function in the form of a metal on a support material comprising one or more ordered mesoporous materials with a unique structure and pore geometry as described below. Preferred ordered mesoporous materials are inorganic, porous, non-layered materials which, in their calcined forms exhibit an X-ray diffraction pattern with at least one peak at a d-spacing greater than about 18 Angstrom Units (Å). They also have a benzene adsorption capacity of greater than 15 grams of benzene per 100 grams of the material at 50 torr and 25° C. In a preferred form, the support material is characterized by a substantially uniform hexagonal honeycomb microstructure with uniform pores having a cell diameter greater than 2 nm and typically in the range of 2 to 50 nm, preferably 3 to 30 nm and most preferably from 3 to 20 nm. Most prominent among these materials is an ordered mesoporous material identified as MCM-41, which is usually synthesized as a metallosilicate with Broensted acid sites by incorporating a tetrahedrally coordinated trivalent element such as Al, Ga, B, or Fe within the silicate framework. The preferred forms of these materials are the aluminosilicates although other metallosilicates may also be utilized. MCM-41 is characterized by a microstructure with a uniform, hexagonal arrangement of pores with diameters of at least about 2 nm: after calcination it exhibits an X-ray diffraction pattern with at least one d-spacing greater than about 18 Å and a hexagonal electron diffraction pattern that can be indexed with a $d_{100}$ value of greater than about 18 Å, which corresponds to the d-spacing of the peak in the X-ray diffraction pattern. This material is described below and in detail in Ser. No. 07/625,245, now U.S. Pat. No. 5,098,684 (Kresge et al) and U.S. Pat. No. 5,102,643 to Kresge et al., both of which are incorporated by reference herein in their entirety.

The ordered mesoporous materials may be crystalline, that is having sufficient order to provide a diffraction pattern such as, for example, by X-ray, electron or neutron diffraction, following calcination, with at least one peak. These mesoporous materials may be characterized by their structure, which includes large pore windows as well as high sorption capacities.

Ordered mesoporous materials as used in the present invention can be distinguished from other porous inorganic solids by the regularity of their large open pores, whose pore size more nearly resembles that of amorphous or paracrystalline materials, but whose regular arrangement and uniformity of size (pore size distribution within a single phase of, for example, +/−25%, usually +/−15% or less of the average pore size of that phase) resemble more those of crystalline framework materials such as zeolites. The term "hexagonal" is intended to encompass not only materials that exhibit mathematically perfect hexagonal symmetry within the limits of experimental measurement, but also those with significant observable deviations from that ideal state. A working definition as applied to the microstructure of the present invention would be that most channels in the material would be surrounded by six nearest neighbor channels at roughly the same distance. Defects and imperfections will cause significant numbers of channels to violate this criterion to varying degrees, depending on the quality of the material's preparation. Samples which exhibit as much as +/−25% random deviation from the average repeat distance between adjacent channels still clearly give recognizable images of the present ordered mesoporous materials.

The ordered mesoporous materials as used for preparation of the catalyst support preferably have the following composition:

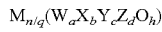

$$M_{n/q}(W_aX_bY_cZ_dO_h)$$

wherein W is a divalent element, such as a divalent first row transition metal, e.g. manganese, cobalt and iron, and/or magnesium, preferably cobalt; X is a trivalent element, such as aluminium, boron, iron and/or gallium, preferably aluminium; Y is a tetravalent element such as silicon and/or germanium, preferably silicon; Z is a pentavalent element, such as phosphorus; M is one or more ions, such as, for example, ammonium, Group IA, IIA and VIB ions, usually hydrogen, sodium and/or fluoride ions; n is the charge of the composition excluding M expressed as oxides; q is the weighted molar 1 average valence of M; n/q is the number of moles or mole fraction of M; a, b, c, and d are mole fractions of W, X, Y and 1 Z, respectively; h is a number of from 1 to 2.5; and (a+b+c+d)=1. A preferred embodiment of the above crystalline material is when (a+b+c) is greater than d, and h=2. A further embodiment is when a and d=0, and h=2. In the as-synthesised form, the mesoporous material has a composition, on an anhydrous basis, expressed empirically as follows:

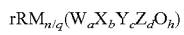

$$rRM_{n/q}(W_aX_bY_cZ_dO_h)$$

wherein R is the total organic material not included in M as an ion, and r is the coefficient for R, i.e. the number of moles or mole fraction of R. The M and R components are associated with the material as a result of their presence during synthesis of the material and are easily removed or, in the case of M, replaced by post-synthesis methods hereinafter more particularly described.

To the extent desired, the original M, e.g. ammonium, sodium or chloride, ions of the as-synthesised material can be replaced in accordance with techniques well known in the art, at least in part, by ion exchange with other ions. Preferred replacing ions include metal ions, hydrogen ions, hydrogen precursor, e.g. ammonium, ions and mixtures thereof. Other ions rare earth metals and metals of Groups IA (e.g. K), IIA (e.g. Ca), VIIA (e.g. Mn), VIIA A (e.g. Ni), IB (e.g. Cu), IIB (e.g. Zn), IIIB (e.g. In), IVB (e.g. Sn), and VIIB (e.g. F) of the Periodic Table of the Elements (Sargent-Welch Co. Cat. No. S-18806, 1979) and mixtures thereof.

The preferred ordered mesoporous materials for use in the process of the present invention are ordered mesoporous silicas. The most preferred ordered mesoporous silicas are those designated as M41S, with the most preferred being MCM-41.

Further examples of ordered mesoporous materials that may be used in the process of the present invention are the mesoporous silicas as described in and prepared according to U.S. Pat. No. 5,951,962, the disclosure of which is incorporated herein in its entirety.

In one embodiment of the present invention the catalyst may consist solely of one or more active hydrogenation metals deposited on the surfaces of one or more ordered mesoporous materials. In this embodiment the catalyst is free of added inorganic binder. The ordered mesoporous material with or without active metal deposited thereon may be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

In a further embodiment the ordered mesoporous materials may be formed into composites with matrix materials resistant to the temperatures and other conditions employed in the hydrogenation process. Such materials include active and inactive materials and synthetic or naturally occurring zeolites as well as inorganic materials such as clays and/or oxides such as alumina, silica or silica-alumina The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. These materials may be incorporated into naturally occurring clays, e.g., bentonite and kaolin, to improve the crush strength of the catalyst under commercial operating conditions and function as binders or matrices for the catalyst. The ordered mesoporous material may be composited with the matrix material in amounts from 99:01 to 05:95 by weight, preferably from 99:01 to 10:90, more preferably from 99:01 to 20:80, and most preferably from 99:01 to 50:50 ordered mesoporous material: matrix material. Preferably, if used the additional matrix material is kept to a minimum typically less than 50 wt % of the combined weight of ordered mesoporous material and matrix material, ideally less than 40 wt %, preferably less than 30 wt %, more preferably less than 20 wt %, more preferably less than 15 wt %, most preferably less than 10 wt % and in a most preferred embodiment less than 5 wt %. Formation of the composition may be achieved by conventional means including mulling the materials together followed by extrusion of pelletizing into the desired finished catalyst particles. Ideally the additional matrix material is macroporous or is a material of mixed porosity i.e. both macroporous and mesoporous. The materials of mixed porosity may have a pore distribution in which from about 5 to about 50%, preferably from about 10 to about 45%, more preferably from about 10 to about 30 and in particular from about 15 to about 25%, of the pore volume is formed by macropores having pore diameters in the range from about 50 nm to about 10,000 nm and from about 50 to about 95%, preferably from about 55 to about 90%, more preferably from about 70 to about 90% and in particular from about 75 to about 85%, of the pore volume is formed by mesopores having a pore diameter of from about 2 to about 50 nm where in each case the sum of the pore volumes adds up to 100%.

When used, the total pore volume of the mixed porosity material is from about 0.05 to 1.5 cm$^3$/g, preferably from 0.1 to 1.2 cm$^3$/g and in particular from about 0.3 to 1.0 cm$^3$/g. The mean pore diameter of the mixed porosity material is preferably from about 5 to 20 nm, preferably from about 8 to about 15 nm and in particular from about 9 to about 12 nm. The surface area of the mixed porosity material is preferably from about 50 to about 500 m$^2$/g, more preferably from about 200 to about 350 m$^2$/g and in particular from about 250 to about 300 m$^2$/g of the support.

The surface area of the macroporous materials and mixed porosity materials may be determined by the BET method using $N_2$ adsorption, in particular in accordance with DIN 66131. The mean pore diameter and the size distribution may be determined by Hg porosimetry, in particular in accordance with DIN 66133.

The macroporous materials and mixed porosity materials that may be used are, for example, macropore containing activated carbon, silicon carbide, aluminum oxide, silicon dioxide, titanium dioxide, zirconium dioxide, magnesium oxide, zinc oxide or mixtures of two or more thereof, with preference being given to using macropore containing alumina.

When an ordered mesoporous material and/or mixed porosity matrix material are used, the finished catalyst may be a composition comprising a support matrix of from 90 to 10% by weight MCM-41 and 10 to 90% by weight alumina, preferably 80 to 20% by weight MCM-41 and 20 to 80% by weight alumina, more preferably 80 to 40% by weight MCM-41 and 20 to 60% by weight of alumina, and as active metal component from 0.01 to 5 wt % Pt, preferably from 0.05 to 1 wt % Pt, more preferably from 0.1 to 0.5 wt % Pt and most preferably 0.15 to 0.4 wt % Pt either alone or in combination with 0.01 to 5 wt % Pd, preferably from 0.05 to 2 wt % Pd, more preferably from 0.1 to 1.5 wt % Pd and most preferably 0.15 to 1.0 wt % Pd. A particularly preferred composition comprises a support matrix of 70 to 60%, ideally 65% by weight MCM-41 and 30 to 40%, ideally 35% by weight alumina, and as active metal component, 0.1 to 0.4, ideally 0.3 wt % Pt alone or in combination with 0.4 to 1.5, ideally 0.9 wt % Pd.

It is preferred that the catalyst used in the present invention comprises one or more active hydrogenation metals deposited on one or more ordered mesoporous support materials free of added inorganic binder material.

The hydrogenation catalyst includes an active metal as the hydrogenation-dehydrogenation component. The hydrogenation-dehydrogenation component is provided by a single metal or combination of metals. Active metals that may be used are preferably one or more metals of transition group VIII of the Periodic Table. Preference is given to using platinum, rhodium, palladium, cobalt, nickel or ruthenium or a mixture of two or more thereof as active metal. A particular preference is given to using ruthenium, platinum, palladium or mixtures of two or more thereof. A particularly preferred active metal is ruthenium.

The content of the metal component will vary according to its catalytic activity. Thus, the highly active noble metals may be used in smaller amounts than the less active base metals. For example, about 1 wt. percent or less palladium or platinum will be effective. The present support materials are, however, notable in that they are capable of including a greater proportion of metal than previous support materials because of their extraordinarily large surface area. The metal component may exceed about 30 percent in a monolayer. The hydrogenation component can be exchanged onto the support material, impregnated into it or physically admixed with it.

The active metal content is generally from about 0.01 to about 30% by weight, preferably from about 0.01 to about 5% by weight and in particular from about 0.1 to about 5% by weight, in each case based on the total weight of the catalyst used. A preferred catalyst is one that comprises ruthenium alone or in combination with one or more additional active metals at a total content of less than 5% by weight of active metal and preferably at a total content of less than 2% by weight of active metal. Preferably the content of ruthenium is from about 0.01 to 2%, more preferably 0.1 to 1% by weight of the total catalyst.

The catalysts according to the present invention may be produced industrially by application of the one or more catalytically active metals to the desired support. The application may be achieved by steeping the support in aqueous metal salt solutions, for example ruthenium or palladium or platinum salt solutions, by spraying appropriate metal salt solutions onto the support or by other suitable methods. Suitable metal salts for preparing the metal salt solutions are the nitrates, nitrosyl nitrates, halides, carbonates, carboxylates, acetylacetonates, chloro complexes, nitrito complexes or ammine complexes of the corresponding metals, with preference being given to the nitrates and nitrosyl nitrates and most preferably the nitrosyl nitrates.

In the case of catalysts, which have a plurality of active metals applied to the support, the metal salts or metal salt solutions can be applied simultaneously or in succession.

When the ordered mesoporous material is used in combination with a matrix material it is preferred that the active hydrogenation metal is applied to the ordered mesoporous material before it is combined with the matrix material.

The ordered mesoporous materials either with or without matrix material, which have been coated or impregnated with the metal salt solution, may subsequently be dried, preferably at from 100 to 150° C. If desired, these supports can be calcined at from 200 to 600° C., preferably from 350 to 450° C.

The dried and/or calcined ordered mesoporous materials either with or without matrix material, are subsequently activated by treatment in a gas stream comprising free hydrogen at from 30 to 600° C., preferably from 100 to 450° C., and in particular from 100 to 300° C. The gas stream preferably consists of from 50 to 100% by volume of $H_2$ and from 0 to 50% by volume of $N_2$.

If a plurality of active metals are applied to the support and the application is carried out in succession, the support can be dried at from 100 to 150° C. and, if desired, calcined at from 200 to 600° C. after each application or impregnation.

Chemisorption measurements are commonly used to estimate the size of supported metal catalysts and metal surface area. The general method for measuring metal surface area by chemisorption is described in J. Lemaitre et al., "Characterization of Heterogenous Catalysts", edited by Francis Delanney, Marcel Dekker, New York (1984), pp. 310-324. The total metal surface area on the catalyst is preferably from 0.01 to 10 $m^2/g$, particularly preferably from 0.05 to 5 $m^2/g$ and more preferably from 0.05 to 3 $m^2/g$ of the catalyst. From chemisorption measurements, the % dispersion (% of metal atoms that populate the surface of the metal particles) can be estimated since a properly chosen titrant used in the chemisorption measurements adsorbs only on metal atoms populating the surface. Consequently higher dispersion values indicate smaller particles with more of the metal atoms populating the surface. For many hydrogenation reactions, activity correlates with dispersion. The preferred method for determining metal dispersion is by using hydrogen as the chemisorption probe molecule under high vacuum static conditions as follows. The sample is held at a temperature of 40° C. and an 8-point isotherm (with pressures between 80 and 400 torr) is obtained using $H_2$ as the chemisorption probe molecule. The linear portion of this isotherm is extrapolated to zero pressure to obtain the total quantity of hydrogen chemisorbed; this is the combined dispersion. The sample is then evacuated at 40° C. to remove any weakly adsorbed hydrogen and the titration repeated to determine what is referred to as weak adsorption isotherm. The linear portion of this weak adsorption isotherm is extrapolated to zero pressure to obtain the quantity of weakly chemisorbed hydrogen. Subtraction of these two values for combined dispersion and weak dispersion yields the strongly held chemisorbed quantity. Thus this method provides values for the total metal dispersion, the dispersion due to weakly chemisorbed hydrogen and dispersion due to strongly chemisorbed hydrogen. The value for the strongly chemisorbed hydrogen is an accurate indication of metal dispersion. In many prior art references the metal dispersion figures provided are based on the total chemisorbed probe and are not split into strong and weak components. In the present invention it is preferred that the hydrogenation catalyst used have dispersion values relating to the strongly chemisorbed component in excess of 20% more preferably in excess of 25% and most preferably in excess of 30%. In addition total dispersion values in excess of 45% preferably in excess of 50%, more preferably in excess of 55%, and most preferably in excess of 60% are achieved. Preferably 40% or more of the total metal dispersion relates to the strongly chemisorbed component, more preferably 45% or more and most preferably 50% or more.

In a further aspect of the present invention prior to deposition of hydrogenation metal on the desired ordered mesoporous support the hydrogenation metal salt solutions used may be combined with one or more amines to form a mixture with the solution and this mixture is applied to the ordered mesoporous support. Preferred amines include alkanolamines such as triethanolamine or amino acids such as L-arginine.

In the process of the present invention, the hydrogenation is generally carried out at from about 50 to 250° C., preferably from about 70 to 220° C., most preferably 75 to 160° C. The pressures used here are generally above 10 bar, more preferably from about 20 to about 300 bar, and most preferably 50 to 300 bar, especially 80 to 300 bar. Preferably the pressure is greater than 100 bar and more preferably greater than 130 bar.

The process of the present invention may be carried out either continuously or batchwise, with preference being given to carrying out the process continuously.

When the process is carried out continuously, the amount of the benzenepolycarboxylic acid or ester to be hydrogenated or of the mixture of two or more thereof is from about 0.05 to about 3 kg per liter of catalyst per hour, preferably from about 0.1 to about 2 kg per liter of catalyst per hour, more preferably from 0.2 to 1.5 kg per liter of catalyst per hour and most preferably from 0.2 to about 1 kg per liter of catalyst per hour.

As hydrogenation gases, it is possible to use any gases which comprise free hydrogen and do not contain harmful amounts of catalyst poisons such as CO, $CO_2$, COS, $H_2S$ and amines. For example, waste gases from a reformer can be used. Preference is given to using pure hydrogen as the hydrogenation gas.

The hydrogenation of the present invention can be carried out in the presence or absence of a solvent or diluent, i.e. it is not necessary to carry out the hydrogenation in solution.

However, preference is given to using a solvent or diluent. Any suitable solvent or diluent may be used. The choice is not critical as long as the solvent or diluent used is able to form a homogeneous solution with the benzenepolycarboxylic acid or ester to be hydrogenated. For example, the solvents or diluents may also comprise water although it is preferred that they are free of water. Examples of suitable solvents or diluents include the following: straight-chain or cyclic ethers such as tetrahydrofuran or dioxane, and also aliphatic alcohols in which the alkyl radical preferably has from 1 to 10 carbon atoms, in particular from 3 to 6 carbon atoms. Examples of alcohols, which are preferably used, are i-propanol, n-butanol, i-butanol and n-hexanol. Mixtures of these or other solvents or diluents can likewise be used.

The amount of solvent or diluent used is not restricted in any particular way and can be selected freely depending on requirements. However, preference is given to amounts which lead to a 10-70% strength by weight solution of the benzenepolycarboxylic acid or ester to be hydrogenated.

In the process of the present invention it is also possible to use one or more derivates of benzenepolycarboxylic acids in the unpurified state that is in the presence of one or more starting materials for their manufacture such as for example alcohol in the case of ester derivatives. Also present may be traces of monoester derivatives, un-reacted acid such as phthalic acid, sodium monoester derivatives and sodium salts of the acids. In this aspect the benzenecarboxylic acid derivative is hydrogenated prior to purification and after hydrogenation is then sent to process finishing for stripping, drying and polishing filtration. In this aspect the benzenecarboxylic acid derivative may be an intermediate feed containing high levels of alcohol in the case of ester derivatives. There may be present 5 to 30% excess alcohol than that required to achieve complete esterification of the acid. In one embodiment there may be an intermediate feed containing 8 to 10 wt % isononyl alcohol in di-isononyl phthalate.

In the process of the present invention the desired products are one or more cyclohexyl materials derived from the hydrogenation of the corresponding benzenepolycarboxylic acid or derivatives thereof. Ideally the benzenepolycarboxylic acid or derivatives thereof are converted to the desired product with a high degree of selectivity and with the maximum conversion possible of the benzenepolycarboxylic acid or derivatives thereof. Hydrogenations of this type often result in undesirable by-products of relatively low molecular weight and low boiling point; these by-products are referred to as "lights". In the context of the present invention "lights" are defined as materials in the as hydrogenated reaction product that are eluted before the object cyclohexyl materials when the as hydrogenated reaction product is analyzed by Gas Liquid Chromatography. Details for one suitable method for determining the "lights" content of a product obtained by the process of the present invention is provided in the specific examples. When using the process of the present invention it is possible to obtain greater than 95% conversion of the starting material (one or more benzenepolycarboxylic acid or derivatives thereof), whilst at he same time producing less than 1.5% by weight based on the total weight of reaction product of "lights". In the process of the present invention the product obtained directly from the hydrogenation reaction ideally contains the object cyclohexyl derivative(s) in an amount that equates to 97 or greater mole % conversion of the starting material, preferably 98.5 or greater mole % conversion, more preferably 99 or greater mole % conversion, and most preferably 99.9 or greater mole % conversion. In the process of the present invention the product obtained directly from the hydrogenation reaction ideally contains 1.3% or less, preferably 1.0% or less, more preferably 0.75% or less, even more preferably 0.5% or less, and in the most preferable embodiment less than 0.3% by weight based on the total weight of the reaction product of "lights". When as hydrogenated products of this level of purity are obtained it may be possible to use these materials directly in certain applications without the need for further purification of the as hydrogenated product such as plasticisers for plastics products.

The process of the present invention is further illustrated by means of the following non-limiting examples.

EXAMPLES

Example 1

Preparation of MCM-41

A sample of MCM-41 (40 Å) was prepared in accordance with the method described below, which corresponds to Example 21 of U.S. Pat. No. 5,837,639. The following mixture (parts by weight-pbw) was charged to an autoclave:

83.7 pbw Cetyltrimethylammonium (CTMA) hydroxide prepared by contacting a 29 wt. % N,N,N-trimethyl-1-hexadecylammonium chloride solution with a hydroxide- for halide exchange resin, 1.7 pbw sodium aluminate, 41.1 pbw tetramethylammonium silicate (10% aqueous solution), and 10.5 pbw precipitated hydrated silica (HiSil)

The mixture was crystallized at 100° C. for 20 hours with stirring under autogeneous pressure. The resulting product was recovered by filtration and dried in air at ambient temperature. The product was then calcined at 540° C. for one hour in nitrogen, followed by six hours in air. The calcined product had a surface area of 1120 m$^2$/g and the following equilibrium adsorption capacities in gram/100 grams:

| | |
|---|---|
| $H_2O$ | 10.8 |
| Cyclohexane | >50 |
| n-Hexane | >50 |
| Benzene | 67 |

The product was identified as MCM-41 with an X-ray diffraction pattern that included a very strong relative intensity line at 38.4+/−2.0 Å, and weak lines at 22.6 +/−1.0, 20.0+/−1.0, and 15.2+/−Å.

Example 2

Preparation of MCM-41

A sample of MCM-41 (40 Å) was prepared in accordance with the following method:

The following mixture (parts by weight-pbw) was charged to an autoclave:

26.8 pbw distilled water, 3.5 pbw Cetyltrimethylammonium (CTMA) chloride (29 wt. % aqueous solution), 4.55 pbw precipitated hydrated silica (Ultrasil PM), 1 pbw Tetramethylammonium hydroxide (25 wt. % aqueous)

The mixture was crystallized at 150° C. for 20 hours with stirring under autogeneous pressure. The resulting product was recovered by filtration and dried in air at ambient temperature. The product was then calcined at 540° C. for one hour in nitrogen, followed by six hours in air. The product was identified as MCM-41. The calcined product has a surface area of 903 m$^2$/g and a pore size (determined by nitrogen adsorption) of 3.8 nm. The analyses are as follows:

| | |
|---|---|
| Silica | 96.8 wt. % |
| Alumina | 0.1018 wt. % |
| Sodium | 0.0300 wt. % |
| Carbon | 0.11 wt. % |

Sorption capacities were as follows:

| | |
|---|---|
| $H_2O$ | 5.9 wt. % |
| Cyclohexane | 53.9 wt. % |
| n-Hexane | 44.1 wt. % |

Example 3

Preparation of Hydrogenation Catalyst—Ruthenium on MCM-41

A solution was prepared by combining with stirring 16.6 grams of ruthenium (III) nitrosyl nitrate aqueous solution with 25.7 grams of triethanolamine and 25.7 grams of distilled water. This solution was added slowly to 25 grams of MCM-41 of Example 2 and dried overnight at 100° C. The catalyst was then calcined to 400° C. for three hours in flowing air. The ruthenium content was a nominal 0.5%.

Example 4

Preparation of Hydrogenation Catalyst—Ruthenium on MCM-41+γ-Alumina

A solution was prepared by combining with stirring 16.6 grams of ruthenium (III) nitrosyl nitrate aqueous solution with 10.7 grams of DI water and 10.7 grams of triethanolamine. This solution was added slowly to 25 grams of 1/16-inch MCM-41 (Example 2) bound with gamma alumina extrudates (65/35 weight % MCM-41/gamma alumina) and dried overnight at 100° C. The catalyst was then calcined to 400° C. for three hours in flowing air. The ruthenium content was a nominal 0.5%.

Example 5

Preparation of Hydrogenation Catalyst—Ruthenium on γ-Alumina

A solution was prepared by combining with stirring 16.6 grams of ruthenium (III) nitrosyl nitrate aqueous solution with 9.0 grams of DI water. This solution was added slowly to 25 grams of 1/16-inch gamma alumina extrudates and dried overnight at 100° C. The catalyst was then calcined to 400° C. for three hours in flowing air. The ruthenium content was a nominal 0.5%.

Example 6

Preparation of Hydrogenation Catalyst—Ruthenium on γ-Alumina

A solution was prepared by combining with stirring 16.6 grams of ruthenium (III) nitrosyl nitrate aqueous solution with 4.2 grams of DI water and 4.2 grams of triethanolamine. This solution was added slowly to 25 grams of 1/16-inch gamma alumina extrudates and dried overnight at 100° C. The catalyst was then calcined to 400° C. for three hours in flowing air. The ruthenium content was a nominal 0.5%.

Example 7

Reduction of Metal Component of Hydrogenation Catalysts

The catalysts used in the hydrogenation of Example 8 were activated under two sets of conditions a) and b) as follows:

a) Catalyst particles (10/20 mesh) were loaded into a stainless-steel catalyst basket then installed in a 300 cm³ autoclave. Metal reduction was conducted under a continuous atmospheric hydrogen flow of ~100 cm³ min⁻¹ at 200° C. for 18 hours.

b) Catalyst particles (10/20 mesh) were loaded into a stainless-steel catalyst basket then installed in a 300 cm³ autoclave. Metal reduction was conducted under a static hydrogen pressure of 1250 psig (approx 86 bar) at 200° C. for 14 hours.

Example 8

Hydrogenation of Di-isononyl Phthalate (DINP)

After activation according to Example 7 the autoclave was cooled. To the cooled autoclave was added 137.4-194.5 g (0.28-0.46 mol) of liquid DINP ((Jayflex DINP (CAS No. 68515-48-0). The autoclave was sealed, heated to the hydrogenation temperature of 80 or 120° C., and pressurized with hydrogen to either a pressure of 840 psig (approx 58 bar) or 3000 psig (approx 207 bar). Hydrogenation was continued for between 3 to 7.5 hrs. At the end of the hydrogenation period the product was analyzed to determine the conversion of DINP and assess the level of lights formation. Conversion of DINP was calculated directly based on the peak areas of residual aromatic proton resonance in 1H NMR spectra. The lights content of the sample was determined by Gas Liquid Chromatography using a DB-1 column (60 m×0.25 mm×0.25 µm), operated at 40-275° C. at a ramp rate of 10° C./min and holding at 275° C. for 35 minutes. The lights were determined as being all product peaks, which eluted in within the first 24.5 minutes. Components eluted thereafter were considered as the desired cyclohexyl products.

The conversions and selectivities for the various hydrogenations are provided in Table 1. This data shows that when MCM-41 is used as the sole catalyst support (Examples 8c and 8e) levels of conversion in excess of 99% may be achieved whilst at the same time resulting in relatively low levels of lights formation. There is also a clear benefit of using a catalyst comprising a mixed support of MCM-41 and alumina when compared to the use of alumina alone as catalyst support. The benefits of using MCM-41 as the sole support are most marked at higher hydrogenation pressures where there is approximately a 50% reduction in lights formation compared to the conventional amorphous alumina supported ruthenium catalysts.

comprising a single metal as a hydrogenation-dehydrogenation component, applied to a catalyst support comprising one or more ordered mesoporous materials, at least one of which materials is ordered mesoporous silica, wherein said ordered mesoporous silica is a metallosilicate.

2. The process as claimed in claim 1 wherein the catalyst support further comprises one or more macroporous materials combined in admixture with the one or more ordered mesoporous materials.

3. The process as claimed in claim 2 wherein the macroporous material is amorphous.

4. The process as claimed in claim 2 wherein the macroporous material is alumina.

5. The process as claimed in claim 4 wherein the catalyst support further comprises one or more mixed porosity materials combined in admixture with the one or more ordered mesoporous materials.

6. The process as claimed in claim 5 wherein the mixed porosity material is amorphous.

7. The process as claimed in claim 5 wherein the mixed porosity material is alumina.

8. The process as claimed in claim 5 wherein the mixed porosity material contains mesopores and macropores.

9. The process as claimed in claim 1 wherein at least one of the ordered mesoporous materials is a material that is synthesized using amphiphilic compounds as directing agents.

10. The process as claimed in claim 9 wherein one or more of the ordered mesoporous materials is selected from the group consisting of materials designated as SBA (Santa Barbara), materials designated as FSM (Folding Sheet Mechanism), materials designated as MSU (Michigan State), materials designated as TMS or Transition Metal Sieves, materials designated as FMMS or Functionalised Monolayers on Mesoporous Supports or materials designated as APM or Acid Prepared Mesostructure or ordered mesoporous materials designated as M41S.

11. The process as claimed in claim 10 wherein the one or more ordered mesoporous materials designated as M41S is are selected from the group consisting of MCM-41, MCM-48 and MCM-50.

12. The process as claimed in claim 11 wherein the ordered mesoporous material is MCM-41.

13. The process as claimed in claim 1 wherein said single metal is selected from transition group VIII of the Periodic Table.

TABLE 1

| Example | Catalyst | Weight DINP (g) | Weight Catalyst (g) | Temp (° C.) | Pressure (psig) | Time (h) | Conversion mole % | Lights (wt %) | Hydrogenation Method |
|---|---|---|---|---|---|---|---|---|---|
| 8a 1 Run | Ru on Al₂O₃ (Ex 6) | 193.6 | 10.0 | 120° | 840 | 7.5 | 97.1 | 0.90 | Example 7b |
| 8b 3 Runs | Ru on MCM-41/Al₂O₃ (Ex 4) | 192.1 | 10.01 | 120° C. | 840 | 7.5 | 97 | 0.74 | Example 7b |
| 8c 2 Runs | Ru on MCM-41 crystal (Ex 3) | 194.5 | 10.0 | 120° C. | 840 | 7.5 | 99+ | 0.44 | Example 7b |
| 8d 2 Runs | Ru on Al₂O₃ (Ex 5) | 154.8 | 8.1 | 120° C. | 3000 | 3 | 96.0 | 0.64 | Example 7a |
| 8e 1 Run | Ru on MCM-41 Crystal (Ex 3) | 137.4 | 6.07 | 120° C. | 3000 | 3 | 99.9+ | 0.35 | Example 7a |

The invention claimed is:

1. A process for hydrogenating, to the corresponding cyclohexyl derivative, one or more benzenepolycarboxylic acids or one or more derivatives thereof, or a mixture of one or more benzenepolycarboxylic acids or one or more derivatives thereof by bringing the benzenepolycarboxylic acid or the derivative thereof or the mixture into contact with a hydrogen-containing gas in the presence of a catalyst, said catalyst 14. The process as claimed in claim 1 wherein said single metal is selected from the group consisting of platinum, rhodium, palladium, cobalt, nickel ruthenium.

15. The process as claimed in claim 1 wherein said single metal is selected from the group consisting of platinum, palladium, and ruthenium.

16. The process as claimed in claim 1 wherein said single metal is ruthenium.

17. The process as claimed in claim 1 wherein said single metal is selected from transition group I or VII of the Periodic Table.

18. The process as claimed in claim 1 wherein said single metal is present in an amount of from 0.01 to 30% by weight, based on the total weight of the catalyst.

19. The process as claimed in claim 2 wherein the one or more macroporous materials have a BET surface area of at most 30 m$^2$/g.

20. The process as claimed in claim 1 wherein the one or more mesoporous materials have a BET surface area of greater than 600 m$^2$/g.

21. The process as claimed in claim 1 wherein the one or more mesoporous materials have a BET surface area of greater than 1000 m$^2$/g.

22. The process as claimed in any claim 1 wherein the metal surface area on the catalyst is from 0.01 to 10 m$^2$/g of the catalyst.

23. The process as claimed in any claim 1 wherein the metal surface area on the catalyst is from 0.05 to 5 m$^2$/g of the catalyst.

24. The process as claimed in claim 1 wherein the metal surface area on the catalyst is from 0.05 to 3 m$^2$/g of the catalyst.

25. The process as claimed in claim 1 wherein said catalyst has a metal dispersion value relating to the strongly chemisorbed component in excess of 20%.

26. The process as claimed in claim 1 wherein said catalyst has a metal dispersion value relating to the strongly chemisorbed component in excess of 25%.

27. The process as claimed in claim 1 wherein said catalyst has a metal dispersion value relating to the strongly chemisorbed component in excess of 30%.

28. The process as claimed in any claim 1 wherein said catalyst has a total metal dispersion value in excess of 45%.

29. The process as claimed in claim 1 wherein said catalyst has a total metal dispersion value in excess of 50%.

30. The process as claimed in claim 1 wherein the hydrogenation catalyst has a total metal dispersion value in excess of 55%.

31. The process as claimed in any claim 1 wherein the one or more benzenepolycarboxylic acids is selected from the group consisting of phthalic acid, terephthalic acid, isophthalic acid, trimellitic acid, trimesic acid, hemimellitic acid and pyromellitic acid and mixtures of two or more thereof.

32. The process as claimed in claim 1 wherein the one or more benzenepolycarboxylic acid derivatives are selected from the group consisting of monoalkyl and dialkyl esters of phthalic acid, terephthalic acid and isophthalic acid, monoalkyl, dialkyl and trialkyl esters of trimellitic acid, trimesic acid and hemimellitic acid, monoalkyl, dialkyl, trialkyl and tetraalkyl esters of pyromellitic acid, anhydrides of phthalic acid, trimellitic acid and hemimellitic acid, pyromellitic dianhydride and mixtures of two or more thereof.

33. The process as claimed in claim 32 wherein the alkyl groups are linear or branched and each group has from 1 to 30 carbon atoms.

34. The process as claimed in claim 32 wherein the alkyl groups are linear or branched and each group has from 2 to 20 carbon atoms.

35. The process as claimed in claim 32 wherein the alkyl groups are linear or branched and each group has from 3 to 18 carbon atoms.

36. The process as claimed in claim 1 wherein the one or more benzenecarboxylic acid derivates are one or more phthalates or isophthalates selected from the group consisting of monomethyl phthalate, dimethyl phthalate, diethyl phthalate, di-n-propyl phthalate, di-n-butyl phthalate, di-tert-butyl phthalate, diisobutyl phthalate, monoglycol esters of phthalic acid, diglycol esters of phthalic acid, di-n-octyl phthalate, diisooctyl phthalate, di-2-ethylhexyl phthalate, di-n-nonyl phthalate, diisononyl phthalate, di-n-decyl phthalate, diisodecyl phthalate, di-n-undecyl phthalate, diisoundecyl phthalate, diisododecyl phthalate, di-n-octadecyl phthalate, diisooctadecyl phthalate, di-n-eicosyl phthalate, monocyclohexyl phthalate, dicyclohexyl phthalate; alkyl isophthalates such as monomethyl isophthalate, dimethyl isophthalate, diethyl isophthalate, di-n-propyl isophthalate, di-n-butyl isophthalate, di-tert-butyl isophthalate, diisobutyl isophthalate, monoglycol esters of isophthalic acid, diglycol esters of isophthalic acid, di-n-octyl isophthalate, diisooctyl isophthalate, di-2-ethylhexyl isophthalate, di-n-nonyl isophthalate, diisononyl isophthalate, di-n-decyl isophthalate, diisodecyl isophthalate, di-n-undecyl isophthalate, di-isoundecyl isophthalate, diisododecyl isophthalate, di-n-octadecyl isophthalate, diisooctadecyl isophthalate, di-n-eicosyl isophthalate, monocyclohexyl isophthalate and dicyclohexyl isophthalate.

37. The process as claimed in claim 1 wherein the one or more benzenecarboxylic acid derivates are one or more terephthalates selected from the group consisting of monomethyl terephthalate, dimethyl terephthalate, diethyl terephthalate, di-n-propyl terephthalate, di-n-butyl terephthalate, di-tert-butyl terephthalate, diisobutyl terephthalate, monoglycol esters of terephthalic acid, diglycol esters of terephthalic acid, di-n-octyl terephthalate, diisooctyl terephthalate, mono-2-ethylhexyl terephthalate, di-2-ethylhexyl terephthalate, di-n-nonyl terephthalate, diisononyl terephthalate, di-n-decyl terephthalate, di-n-undecyl terephthalate, diisodecyl terephthalate, diisoundecyl terephthalate, diisododecyl terephthalate, di-n-octadecyl terephthalate, diisooctadecyl terephthalate, di-n-eicosyl terephthalate, ditridecyl terephthalate, diisotridecyl terephthalate, monocyclohexyl terephthalate and dicyclohexyl terephthalate.

38. The process as claimed in claim 1 wherein the one or more benzenecarboxylic acid derivates are one or more alkyl trimellitates selected from the group consisting of such as monomethyl trimellitate, dimethyl trimellitate, diethyl trimellitate, di-n-propyl trimellitate, di-n-butyl trimellitate, di-tert-butyl trimellitate, diisobutyl trimellitate, the monoglycol ester of trimellitic acid, diglycol esters of trimellitic acid, di-n-octyl trimellitate, diisooctyl trimellitate, di-2-ethylhexyl trimellitate, di-n-nonyl trimellitate, diisononyl trimellitate, di-n-decyl trimellitate, diisodecyl trimellitate, di-n-undecyl trimellitate, diisoundecyl trimellitate, diisododecyl trimellitate, di-n-octadecyl trimellitate, diisooctadecyl trimellitate, di-n-eicosyl trimellitate, monocyclohexyl trimellitate, dicyclohexyl trimellitate and trimethyl trimellitate, triethyl trimellitate, tri-n-propyl trimellitate, tri-n-butyl trimellitate, tri-tert-butyl trimellitate, triisobutyl trimellitate, triglycol esters of trimellitic acid, tri-n-octyl trimellitate, triisooctyl trimellitate, tri-2-ethylhexyl trimellitate, tri-n-nonyl trimellitate, tri-isononyl trimellitate, tri-n-decyl trimellitate, triisododecyl trimellitate, tri-n-undecyl trimellitate, tri-isoundecyl trimellitate, triisododecyl trimellitate, tri-n-octadecyl trimellitate, triisooctadecyl trimellitate, tri-n-eicosyl trimellitate and tri-cyclohexyl trimellitate.

39. The process as claimed in claim 1 wherein the one or more benzenecarboxylic acid derivates are one or more alkyl trimesates selected from the group consisting of monomethyl trimesate, dimethyl trimesate, diethyl trimesate, di-n-propyl trimesate, di-n-butyl trimesate, di-tert-butyl trimesate, diisobutyl trimesate, monoglycol esters of trimesic acid, diglycol esters of trimesic acid, di-n-octyl trimesate, diisooctyl trimesate, di-2-ethylhexyl trimesate, di-n-nonyl trimesate, diisononyl trimesate, di-n-decyl trimesate, diisodecyl trimesate, di-n-undecyl trimesate, di-isoundecyl trimesate, diisododecyl trimesate, di-n-octadecyl trimesate, diisooctadecyl trimesate, di-n-eicosyl trimesate, monocyclohexyl trimesate, dicyclohexyl trimesate, and also trimethyl trimesate, triethyl trimesate, tri-n-propyl trimesate, tri-n-butyl trimesate, tri-tert-butyl trimesate, triisobutyl trimesate, triglycol esters of trimesic acid, tri-n-octyl trimesate, triisooctyl trimesate, tri-2-ethyl-hexyl trimesate, tri-n-nonyl trimesate, tri-isononyl trimesate, tri-n-decyl trimesate, triisododecyl trimesate, tri-n-undecyl trimesate, tri-isoundecyl trimesate, triisododecyl trimesate, tri-n-octadecyl trimesate, triisooctadecyl trimesate, tri-n-eicosyl trimesate and tricyclohexyl trimesate.

40. The process as claimed in claim 1 wherein the one or more benzenecarboxylic acid derivates are one or more alkyl hemimellitates selected from the group consisting of monomethyl hemimellitate, dimethyl hemimellitate, diethyl hemimellitate, di-n-propyl hemimellitate, di-n-butyl hemimellitate, di-tert-butyl hemimellitate, diisobutyl hemimellitate, monoglycol esters of hemimellitic acid, diglycol esters of hemimellitic acid, di-n-octyl hemimellitate, diisooctyl hemimellitate, di-2-ethylhexyl hemimellitate, di-n-nonyl hemimellitate, diisononyl hemimellitate, di-n-decyl hemimellitate, diisodecyl hemimellitate, di-n-undecyl hemimellitate, di-isoundecyl hemimellitate, diisododecyl hemimellitate, di-n-octadecyl hemimellitate, diisooctadecyl hemimellitate, di-n-eicosyl hemimellitate, monocyclohexyl hemimellitate, dicyclohexyl hemimellitate, and also trimethyl hemimellitate, triethyl hemimellitate, tri-n-propyl hemimellitate, tri-n-butyl hemimellitate, tri-tert-butyl hemimellitate, triisobutyl hemimellitate, triglycol esters of hemimellitic acid, tri-n-octyl hemimellitate, triisooctyl hemimellitate, tri-2-ethylhexyl hemimellitate, tri-n-nonyl hemimellitate, tri-isononyl hemimellitate, tri-n-decyl hemimellitate, triisodecyl hemimellitate, tri-n-undecyl hemimellitate, tri-isoundecyl hemimellitate, triisododecyl hemimellitate, tri-n-octadecyl hemimellitate, triisooctadecyl hemimellitate, tri-n-eicosyl hemimellitate and tricyclohexyl hemimellitate.

41. The process as claimed in claim 1 wherein the one or more benzenecarboxylic acid derivates are one or more alkyl pyromellitates selected from the group consisting of monomethyl pyromellitate, dimethyl pyromellitate, diethyl pyromellitate, di-n-propyl pyromellitate, di-n-butyl pyromellitate, di-tert-butyl pyromellitate, diisobutyl pyromellitate, monoglycol esters of pyromellitic acid, diglycol esters of pyromellitic acid, di-n-octyl pyromellitate, diisooctyl pyromellitate, di-2-ethylhexyl pyromellitate, di-n-nonyl pyromellitate, diisononyl pyromellitate, di-n-decyl pyromellitate, diisodecyl pyromellitate, di-n-undecyl pyromellitate, di-isoundecyl pyromellitate, diisododecyl pyromellitate, di-n-octadecyl pyromellitate, diisooctadecyl pyromellitate, di-n-eicosyl pyromellitate, monocyclohexyl pyromellitate, trimethyl pyromellitate, triethyl pyromellitate, tri-n-propyl pyromellitate, tri-n-butyl pyromellitate, tri-tert-butyl pyromellitate, triisobutyl pyromellitate, triglycol esters of pyromellitic acid, tri-n-octyl pyromellitate, triisooctyl pyromellitate, tri-2-ethylhexyl pyromellitate, tri-n-nonyl pyromellitate, tri-isononyl pyromellitate, triisodecyl pyromellitate, tri-n-decyl pyromellitate, tri-n-undecyl pyromellitate, tri-isoundecyl pyromellitate, triisododecyl pyromellitate, tri-n-octadecyl pyromellitate, triisooctadecyl pyromellitate, tri-n-eicosyl pyromellitate, tricyclohexyl pyromellitate, and also tetramethyl pyromellitate, tetraethyl pyromellitate, tetra-n-propyl pyromellitate, tetra-n-butyl pyromellitate, tetra-tert-butyl pyromellitate, tetraisobutyl pyromellitate, tetraglycol esters of pyromellitic acid, tetra-n-octyl pyromellitate, tetraisooctyl pyromellitate, tetra-2-ethylhexyl pyromellitate, tetra-n-nonyl pyromellitate, tetraisododecyl pyromellitate, tetra-n-undecyl pyromellitate, tetraisododecyl pyromellitate, tetra-n-octadecyl pyromellitate, tetraisooctadecyl pyromellitate, tetra-n-eicosyl pyromellitate and tetracyclohexyl pyromellitate.

42. The process as claimed in claim 1 wherein the one or more benzenecarboxylic acid derivates are one or more derivates selected from the group consisting of alkyl terephthalates, alkyl phthalates, alkyl isophthalates, dialkyl trimellitates, trialkyl trimellitates, dialkyl trimesates, trialkyl trimesates, dialkyl hemimellitates, trialkyl hemimellitates, dialkyl pyromellitates, trialkyl pyromellitates and tetraalkyl pyromellitates, in which one or more of the alkyl groups contain 5, 6 or 7 carbon atoms.

43. The process as claimed in claim 1, wherein the hydrogenation is carried out in the presence of a solvent or diluent.

44. The process as claimed in claim 1, wherein the hydrogenation is carried out continuously.

45. The process as claimed in claim 16, further comprising a second single metal, other than ruthenium, selected from transition group VIII of the Periodic Table.

* * * * *